US008777414B2

(12) United States Patent
Spratt et al.

(10) Patent No.: US 8,777,414 B2
(45) Date of Patent: Jul. 15, 2014

(54) PUPIL DEPENDENT WAVEFRONT REFRACTION

(71) Applicants: Carl Zeiss Vision Inc., San Diego, CA (US); Carl Zeiss Vision International GmbH, Aelen (DE)

(72) Inventors: Ray Steven Spratt, Petaluma, CA (US); Timo Kratzer, Aalen (DE); Jesús-Miguel Cabeza-Guillén, Aalen (DE)

(73) Assignee: Carl Zeiss Vision Inc., San Diego, CA (US)

(*) Notice: Subject to any disclaimer, the term of this patent is extended or adjusted under 35 U.S.C. 154(b) by 98 days.

(21) Appl. No.: 13/721,471

(22) Filed: Dec. 20, 2012

(65) Prior Publication Data

US 2014/0078464 A1 Mar. 20, 2014

Related U.S. Application Data

(63) Continuation of application No. PCT/US2010/050658, filed on Sep. 29, 2010.

(60) Provisional application No. 61/365,028, filed on Jul. 16, 2010.

(51) Int. Cl.
*A61B 3/00* (2006.01)
*A61B 3/10* (2006.01)

(52) U.S. Cl.
CPC ............. *A61B 3/1015* (2013.01); *A61B 3/0025* (2013.01)
USPC .......................................................... 351/246

(58) Field of Classification Search
USPC .......................................................... 351/246
See application file for complete search history.

(56) References Cited

U.S. PATENT DOCUMENTS 6,199,986 B1 3/2001 Williams et al.
(Continued)

FOREIGN PATENT DOCUMENTS

WO WO 2004/053568 6/2004
WO WO 2004/086952 10/2004

OTHER PUBLICATIONS

The International Preliminary Report on Patentability from the counterpart PCT Application No. PCT/US2010/050658, dated Jan. 22, 2013.

(Continued)

*Primary Examiner* — Jordan Schwartz
(74) *Attorney, Agent, or Firm* — Fish & Richardson P.C.

(57) ABSTRACT

A method of determining an ophthalmic prescription (Rx) for a patient's eye, includes obtaining a wavefront measurement of the patient's eye; determining a first Rx for the patient's eye from the wavefront measurement, the first Rx corresponding to a maximum value of a merit function calculated from the wavefront measurement of the patient's eye for a first size of the pupil of the patient's eye; determining one or more additional Rx's of the patient's eye for one or more additional pupil sizes different from the first pupil size, wherein each additional Rx is determined for a corresponding size by calculating a value of the merit function for the previously-calculated Rx at the corresponding size and searching for an Rx at the corresponding size that provides a larger value of the merit function than the previously-calculated Rx at the corresponding size; determining a final Rx based on the first Rx and the additional Rx's; and outputting the final Rx.

25 Claims, 15 Drawing Sheets

(56) References Cited

U.S. PATENT DOCUMENTS

| | | | | |
|---|---|---|---|---|
| 7,029,119 | B2 | 4/2006 | Youssefi et al. | |
| 7,077,522 | B2 | 7/2006 | Williams | |
| 7,744,217 | B2 | 6/2010 | Cabeza et al. | |
| 2004/0169820 | A1 | 9/2004 | Dai et al. | |
| 2005/0213040 | A1 | 9/2005 | Gross et al. | |
| 2009/0079940 | A1* | 3/2009 | Dai et al. | 351/246 |
| 2010/0039614 | A1* | 2/2010 | Morris et al. | 351/205 |
| 2011/0211162 | A1* | 9/2011 | Thibos et al. | 351/221 |

OTHER PUBLICATIONS

Thibos et.al., *Accuracy and Precision of Objective Refraction for Wavefront Aberrations*, Journal of Vision (2004) 4, 329-351.

William H. Press, et al., Numerical Recipes in C: The Art of Scientific Computing, 2nd Edition, Cambridge University Press, Chapter 10.3, 1992.

The International Search Report and a Written Opinion from the counterpart PCT Application No. PCT/US2010/050658, dated Mar. 23, 2011.

* cited by examiner

PUPIL DEPENDENT WAVEFRONT REFRACTION

CROSS-REFERENCE TO RELATED APPLICATIONS

This application is a continuation of, and claims benefit under 35 USC 120 to, international application PCT/US2010/050658, filed Sep. 29, 2010, which claims benefit under 35 USC 119(e) of U.S. Ser. No. 61/365,028, filed Jul. 16, 2009. Both applications are incorporated by reference herein in their entirety.

TECHNICAL FIELD

This disclosure relates to wavefront refractions and methods including the same.

BACKGROUND

Wavefront aberration measurements can be used to determine defects in a patient's vision. The correction of vision defects can be expressed by an ophthalmic prescription (Rx), which includes three parameters that correct second order aberrations of a patient's vision. The three parameters can be represented by values for sphere, cylinder, and cylinder axis. Conventional methods, e.g., as described in U.S. Pat. Nos. 7,029,119, 7,077,522, and 7,744,217, calculate the Rx based only on a single fixed pupil size for the eye.

SUMMARY

In certain aspects, the invention features methods for obtaining an Rx that involve refraction at more than one pupil size. In some embodiments, this involves searching a multi-dimensional parameter space for optimal values for the Rx at each of several different pupil sizes.

In embodiments, the search can be performed by starting with an Rx determined for a smallest pupil size, then tracking the movement (in Rx space) of that extremum corresponding to the small-pupil Rx as the aperture is increased. Typically, the Rx space is a three dimensional space spanned by the second order corrections—sphere, cylinder and cylinder axis.

A final Rx is determined based on the tracked extrema in Rx space. In general, the Rx can correspond to an extremum at a particular pupil size (e.g., for the largest pupil size or some intermediate pupil size) or can correspond to some other Rx determined based on the extrema. Determining the Rx based on the full data set may advantageously provide a vision correction that works well over a range of pupil diameters, rather than just for a single large pupil.

In some embodiments, a variation in the algorithm is the size of the step in pupil diameter between consecutive Rx determinations.

The calculation of the Rx can be refined by including physiological aspects such as the Stiles-Crawford effect. This effect may be accounted for by an apodization that gives a lower weighting to peripheral rays in the merit function.

Further physiological aspects might be taken into consideration. For instance, many subjects prefer astigmatic corrections whose axis is either at 0 or 90 degrees. The search algorithm can be improved, in that those axis positions are given a higher weighting. This means, for example, if the optimum astigmatism axis is at 3 degrees but the difference in the merit function to another astigmatism correction at 0 degrees is below a certain threshold, the astigmatism correction at 0 degree would be preferred in the final Rx.

In some embodiments, the input wavefront aberrations of the eye are measured for a sufficiently large pupil using appropriate means. The wavefront aberration for small pupil can then be obtained by mathematically cropping the measured wavefront aberration for a large pupil (resizing). In some embodiments, the wavefront aberration can be measured for a set of pupil sizes. In this way a set of actually measured wavefront aberrations are obtained for a set of pupil sizes that can be used directly when searching for an Rx without the need of mathematical cropping. Both approaches can also be combined. Measuring the wavefront aberration for a set of pupil sizes has another advantage in the actual measured pupil form can be used in the calculation, giving more accurate results than, e.g., if a circular pupil is assumed.

In some cases it may be desired to obtain a final Rx that is tailored for smaller pupil sizes (daylight lens) or for larger pupil sizes (night lens). This can be accomplished, for example, by more strongly weighting the Rx values for a specific pupil size range when determining the final Rx.

Various aspects of the invention are summarized as follows.

In general, in one aspect, the invention features a method of determining an ophthalmic prescription (Rx) for a patient's eye, including obtaining a wavefront measurement of the patient's eye; determining a first Rx for the patient's eye from the wavefront measurement, the first Rx corresponding to a maximum value of a merit function calculated from the wavefront measurement of the patient's eye for a first size of the pupil of the patient's eye; determining one or more additional Rx's of the patient's eye for one or more additional pupil sizes different from the first pupil size, wherein each additional Rx is determined for a corresponding size by calculating a value of the merit function for the previously-calculated Rx at the corresponding size and searching for an Rx at the corresponding size that provides a larger value of the merit function than the previously-calculated Rx at the corresponding size; determining a final Rx based on the first Rx and the additional Rx's; and outputting the final Rx.

Implementations of the invention can include one or more of the following features. For example, each Rx can be calculated for the same location of the patient's eye. This location can be a central location of the patient's eye.

The first size can be a smaller size than the one or more additional sizes. In some embodiments, the smallest size is 0.1 mm or less. The sizes can span a range from less than 0.1 mm to 5 mm (e.g., to 4 mm, to 3 mm). The sizes can be increased in increments of 0.5 mm or less (e.g., 0.4 mm or less, 0.3 mm or less, 0.2 mm or less, 0.1 mm or less, 0.05 mm or less).

Each of the one or more additional Rx's can be determined for a pupil size that is larger than the size used to calculate the prior Rx.

The method can include ordering an eyeglass lens or contact lens for the patient based on the final Rx. The method can include making an eyeglass lens or contact lens for the patient based on the final Rx.

Calculating the Rx's can include accounting for one or more physiological aspects of the patient's eye. For example, one of the physiological aspects can be the Stiles-Crawford effect. One of the physiological aspects can be accounting for a preferential axis orientation. The preferential axis orientation can be 0 degrees or 90 degrees. Accounting for the preferential axis orientation can include weighting the orientation more heavily than other orientations in the search algorithm.

The wavefront measurement can include information about the wavefront aberrations of the eye. The wavefront measurement for the patient's eye can be measured for a pupil that has a relatively large size compared to the first size.

Obtaining the wavefront measurement can include obtaining a wavefront measurement for a pupil that has a relatively large size compared to the first size, and modifying the wavefront measurement to correspond to smaller size pupil.

Obtaining the wavefront measurement can include obtaining a plurality of wavefront measurements of the eye each corresponding to a different pupil size.

The final Rx can be the Rx corresponding to the largest pupil size. In some embodiments, determining the final Rx includes calculating an Rx based on the first Rx and additional Rx's. At least some of the first Rx and the additional Rx's can be weighted differently in the calculation of the final Rx. The Rx's can be weighted based on anticipated use of the Rx by the patient.

The merit function can correspond to a metric related to a caustic of a light ray passing through a corrective optic and the eye.

Outputting the final Rx can involve transmitting an electronic file (e.g., an e-mail) that contains the Rx, printing the Rx, and/or displaying the Rx (e.g., on an electronic display).

In general, in a further aspect, the invention features a non-transitory computer readable storage medium encoded with executable instructions including instructions operable on a processor to determine a first ophthalmic prescription (Rx) for a patient's eye from a wavefront measurement of the patient's eye, the first Rx corresponding to a maximum value of a merit function calculated from the wavefront measurement for the patient's eye for a first size of the pupil of the patient's eye; instructions operable on a processor to determine one or more additional Rx's for the patient's eye for one or more additional pupil sizes different from the first pupil size, wherein each additional Rx is determined for a corresponding size by calculating a value of the merit function for the previously-calculated Rx at the corresponding size and searching for an Rx at the corresponding size that provides a larger value of the merit function than the previously-calculated Rx at the corresponding diameter; instructions operable on a processor to determine a final Rx based on the first Rx and the additional Rx's; and instructions operable on a processor to output the final Rx.

Embodiments of the non-transitory computer readable storage medium can be encoded with instructions in accordance with features of other aspects.

In a further aspect, the invention features a system for determining a prescription (Rx) for a patient's eye, the system including a processor, and the non-transitory computer readable storage medium encoded with executable instructions of the foregoing aspect, wherein during operation the processor executes the instructions stored on the storage medium and the system outputs the final Rx.

Among other advantages, embodiments of the invention can eliminate ambiguity caused by multiple local extrema in a merit function in a multi-dimensional parameter space. As a result, the methods can be used to identify an optimal Rx efficiently by eliminating non-optimal local extrema.

The selection metric used in conventional algorithms can suffer from instability which leads to multiple local extrema in the merit function having nearly equal merit values. As a result, the selection of a particular extremum may be determined by chance (i.e., an artifact of where the search was started), or numerical jitter. These issues can be avoided using the methods disclosed herein.

The details of one or more embodiments of the invention are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

Methods for determining an Rx by evaluating a merit function for the vision correction over a multi-dimensional space are disclosed. In general, a merit function will exhibit multiple local extrema across a multi-dimensional space and conventional search algorthims can inadvertently identify solutions (local extrema of the merit function) that do not correspond to a best or optimal vision correction. In embodiments of the method, the search is guided by a "best" Rx, which is established for a subset of the parameter space (e.g., for a particular pupil size) where a unique solution exists. The method then establishes solutions at other regions of the parameter space based on the best Rx, allowing one to identify solutions more efficiently than searching in an essentially unrestricted multi-dimensional space.

In certain embodiments, the method involves evaluating a merit function over a five dimensional space—three dimensions of which are the three Rx parameters: sphere, cylinder and cylinder axis, the other two dimensions are the x- and y-coordinates of the point spread function (details of which are provided below). An Rx is established for a smallest pupil size, for which the solution for the Rx is unique. Here, the pupil size refers to the maximum dimension of the pupil of the eye. For a circular pupil, the size refers to the pupil diameter. Subsequently, Rx's are determined at larger pupil sizes using a hill-climbing algorithm to identify local extrema in the merit function at the larger pupil sizes, where the starting point at each pupil size is the Rx of the prior pupil size. This procedure automatically provides the optimum Rx information for the full range of pupil sizes. It can also resolve the issue of distinguishing between multiple peaks at large pupil sizes, since the unique peak that smoothly degenerates into the small aperture solution is automatically selected.

Figure 1:
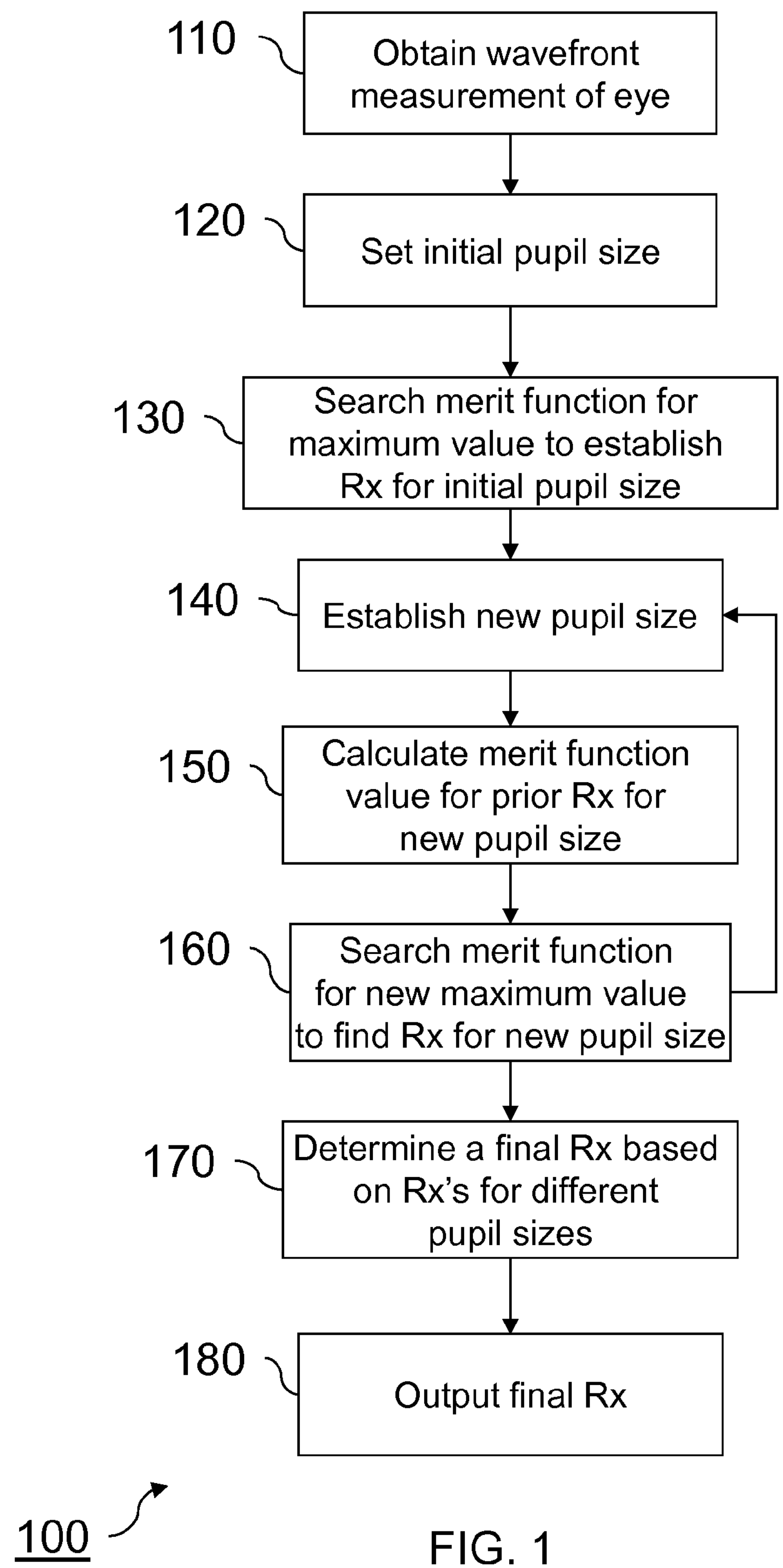
FIG. 1 is a flow chart summarizing an embodiment of a method for determining an Rx for an eye.

FIG. 1 shows a flow chart summarizing a method 100 for determining an Rx. Here, a single wavefront aberration measurement of an eye is made using appropriate means at the largest pupil size for which the Rx is to be determined. Rx's for different pupil sizes are determined by apodizing the measured wavefront aberration to the desired pupil size for which an Rx is to be calculated. In other words, a single wavefront refraction is performed from which Rx's at different pupil sizes can be calculated.

Specifically, the steps of method 100 are as follows. First, one obtains a wavefront measurement of the eye (step 110). In general, wavefront measurements can be performed in a variety of ways. For example, in some embodiments, wavefront measurements can be performed using the Shack-Hartmann method, the Tscherning method, the ray-tracing method or by tomography measurements of the eye.

In the Shack-Hartmann method, a light ray is projected on the retina of the eye. In the Tscherning method, a light point pattern is projected on the retina. The path of the reflected ray in the optical system is investigated and any changes in the direction of the rays (in the case of the Shack-Hartmann method) or a deviation of the image from the original pattern (in the case of the Tscherning method) after leaving the optical system are registered. The deviation of the profile of the measured wavefront from the ideal case is referred to as aberration and can be measured with an aberrometer.

In a ray-tracing method, a very fine laser beam is directed through the pupil of the eye and scanned over the retina. Each laser point may be identified as a reflection on the macula. The position and shape of this image on the macula provide information about vision quality. In tomography, the geometries of the surfaces of the eye that perform an optical function are measured.

In general, a variety of devices, such as a wavefront sensor (e.g., aberrometer), can be used for measuring wavefronts. Wavefront sensors are available commercially from Abbott Medical Optics (Santa Ana, Calif.), Carl Zeiss Meditec (Dublin, Calif.), and Alcon (Fort Worth, Tex.), for example.

In step 120, an initial pupil size is set in order to determine an initial Rx. This involves apodizing the data obtained from the wavefront measurement to limit the data so that it corresponds to the initial pupil size. Typically, this is the smallest pupil size for which an Rx is to be determined. At this pupil size, an Rx can be determined unambiguously because, in general, a merit function will contain only a single extremum so the search algorithm will not return a false result. Generally, the initial pupil size can vary as desired. In some embodiments, the initial pupil size (e.g., diameter) is in a range from 0.0 mm to 2 mm.

In step 130, the Rx for the measured wavefront aberration is established for the initial pupil size by searching for the maximum value in a merit function for each of the parameters of Rx. For shorthand, this Rx is referred to as "$Rx_1$" below.

In general, a variety of merit functions can be used. Exemplary metrics are disclosed in Thibos et. al., *Accuracy and Precision of Objective Refraction for Wavefront Aberrations*, Journal of Vision (2004) 4, 329-351. Metrics can be categorized in two different classes: those that are derived directly from the measured wavefront aberration (e.g., wavefront quality metrics as disclosed by Thibos et al.), and those that are derived from an estimate of the focused beam at and around the retina (e.g., image quality metrics as disclosed by Thibos et al.). Examples of wavefront quality metrics include metrics that evaluate an RMS wavefront error over at least a portion of the pupil.

In some embodiments, the merit function is a normalized intensity of an image in the center of a point-spread function.

The merit function may also account for physiological effects such as the Stiles-Crawford effect in which a smaller weight is given to peripheral rays in the merit function.

Exemplary merit functions are disclosed, for example, in U.S. Pat. No. 7,744,217, the contents of which are incorporated herein by reference in their entirety. For example, the merit function can involve determining, for each set of values within the Rx space being searched, evaluates the relationship between a caustic of a light beam passing through an ophthalmic lens have the Rx and the retina of the eye. The term "caustic" in this context means the narrow constriction that occurs instead of an image point as a result of imaging errors for a light bundle originating from an object point before it spreads out again. The value of the metric can be related to the distance between the caustic and the retina, with a higher metric value corresponding to a closer distance.

Further, a variety of search algorithms can be used. For example, the search algorithm can be a hill-climbing algorithm, a random walk algorithm, or a simulated annealing algorithm. Exemplary search algorithms are disclosed in Numerical Recipes in C: The Art of Scientific Computing," $2^{nd}$ Edition, William H. Press, et al., Cambridge University Press (1992).

In step 140, the wavefront aberration measured at step 110 is apodized to a new pupil size larger than the initial pupil size. In general, the difference between the new pupil size and the initial pupil size can vary. If the size of the step is too large, there is a danger that $Rx_1$ will be closer to a non-optimum local extremum of the merit function at the new pupil size that the optimum local extremum and an incorrect value of the Rx at the new pupil size will be identified. If the size of the step is too small, however, computation time may be unnecessarily increased. In some embodiments, the new pupil size (e.g., diameter) is in a range from 0.1 mm to 1 mm larger than the initial pupil size (e.g., diameter). For example, the difference in pupil diameters can be about 0.1 mm, about 0.2 mm, about 0.3 mm, about 0.4 mm, or about 0.5 mm.

In step 150, the value of the merit function for $Rx_1$ is calculated for the new pupil size. This value for the merit function is the starting position for the search algorithm for establishing an Rx for the new pupil size (step 160). As in the determination of $Rx_1$, the search algorithm is used to identify a maximum value for the merit function at the new pupil size. Using the same shorthand, the method thus establishes an Rx, $Rx_2$, for the second pupil size.

Step 140 through step 160 are repeated as the pupil size is increased, each time the method providing an Rx, $Rx_i$, for the i-th pupil size. Increments between subsequent pupil sizes (e.g., diameters) can be the same or different. These increments can be in the range cited above between the first and second pupil sizes.

In some embodiments, as the size of the pupil increases, the step size to the next size may decrease so that the incremental change in the area of the pupil between each step is the same.

As mentioned previously, it is believed that there is no ambiguity in determining a correct second order correction for the wavefront aberrations of an eye for a pupil with a size approaching zero. Thus, it is believed that the Rx established for the smallest pupil size, $Rx_1$, unambiguously establishes an optimal Rx at that pupil size. As the pupil size is increased, the merit function is computed only for a small range of values starting at the previously-established Rx, and extending in the direction of increasing value of the merit function at the current pupil size. The search terminates when the search algorithm finds a maximum value of the merit function. The search algorithm does not need to evaluate the merit function in the parameter space outside the range bounded by the starting value found for the previous (smaller) pupil size and the maximum value of the merit function.

When Rx's for the full set of desired pupil sizes has been established, the method determines a final Rx based on the $Rx_i$'s. This can involve selecting an Rx for a specific pupil size, which can correspond to one of the pupil sizes for which Rx's were calculated or by interpolating the Rx's. In general, the specific pupil size can correspond to certain conditions. For example, the final Rx can be selected for a relatively small pupil size, corresponding, e.g., to high ambient light level conditions (e.g., bright sunlight). Alternatively, the specific pupil size can correspond to low light levels (e.g., for night vision). Intermediate pupil sizes can also be considered.

In some embodiments, the final Rx corresponds to an Rx that performs best, on average, over the full range of pupil diameters. For example, the final Rx can be some average (e.g., a weighted average) of the Rxs at different pupil sizes. Averaging the Rxs can involve weighting Rxs based on an anticipated use of the Rx by the patient (e.g., for daylight use, for nighttime use, for reading, for driving, for use with a computer). In some embodiments, the peak merit function value at each pupil size is used to determine relative weightings of the different Rxs when calculating the final Rx. For example, an Rx corresponding to a higher merit function value can be weighted more heavily than an Rx corresponding to a lower merit function value.

Method 100 terminates at step 180 when the final Rx is output.

While method 100 involves a single wavefront measurement of the eye, other implementations are also possible. For example, referring to FIG. 2, in some embodiments a method 200 involves physically, rather than mathematically, vary the pupil size and making a series of refractions at each pupil size. Method 200 starts at step 210 with setting an initial pupil size. The initial pupil size is the smallest pupil size for which Rx is to be determined. The physical pupil size can be varied, for example, by changing the ambient light level at which the measurement is made and/or by stopping down the aperture over which the eye is illuminated during the measurement using an external (to the eye) aperture stop.

At step 220, a wavefront measurement of a patient's eye is made at the set initial pupil size and a corresponding Rx established (step 230). In step 240, the size of the pupil is increased and a new wavefront measurement is made (step 250) at the new pupil size. The method calculates a value for the merit function at the new pupil size for $Rx_1$ (step 260), and a search algorithm is used to determine an optimum Rx for the new pupil size in the same way as described above for method 100 (step 270). Step 240 to step 270 are repeated until the full set of pupil-dependent Rxs are determined for all desired pupil sizes. In step 280, a final Rx based on the full set of Rx determined at each of the desired pupil sizes is computed. Method 200 terminates at step 290 with the output of the final Rx.

Figure 2:
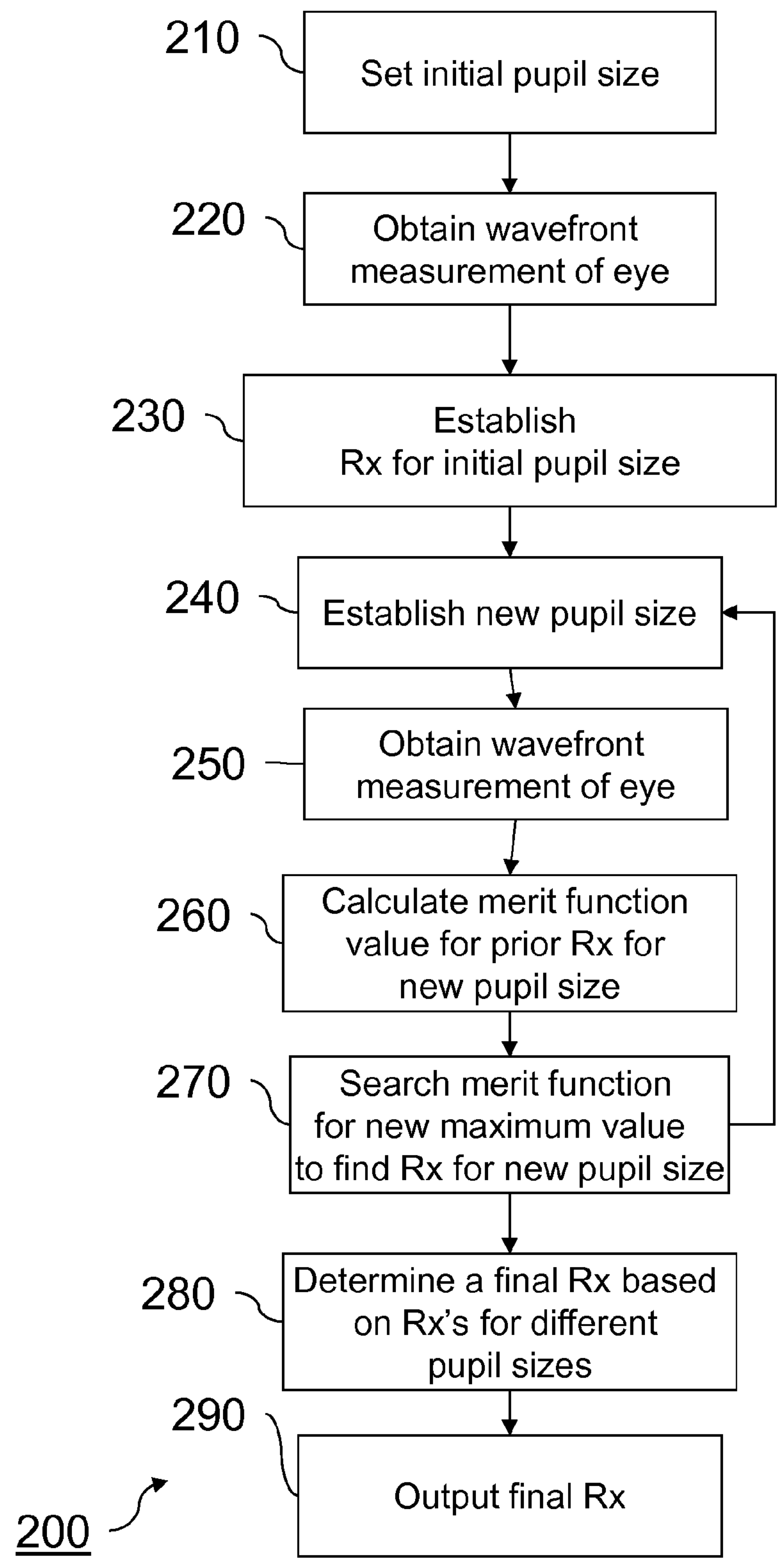
FIG. 2 is a flow chart summarizing another embodiment of a method for determining an Rx for an eye.

In some embodiments, the approaches shown in FIGS. 1 and 2 may be combined. For example, one can take wavefront measurements of the eye for multiple different physical pupil sizes, but then apodize one or more of the measurements, e.g., to provide the same pupil shape for calculating each Rx. For example, the data from each measurement can be apodized to provide pupil shape (e.g., a circular pupil shape) optimized for the merit function.

The methods can involve additional parameters. For example, in some embodiments, the methods can be applied at different wavelengths and the final Rx determined accordingly. For example, the wavefront measurement can be performed at one wavelength and the analysis performed at one or more different wavelengths (e.g., by accounting for dispersion in the optical system). In some embodiments, the wavefront measurement is made using infrared radiation, while the analysis is performed at one or more visible wavelengths corresponding to different viewing conditions. For example, analysis can be performed at conditions emulating daytime vision (e.g., at a wavelength of 555 nm) and for nighttime vision (e.g., 507 nm). In certain embodiments, the analysis wavelength is varied as a function of pupil diameter to better represent peak sensitivity for expected light conditions for the various pupil sizes. For example, Rxs can be calculated at smaller pupil sizes for daytime vision and for larger pupil sizes for nighttime vision in addition to making the wavelength adjustments.

In some embodiments, such methods can include obtaining wavefront measurements at different wavelength, e.g., by filtering the light used to make the wavefront measurement or by using different light sources.

Accordingly, Rx values can be established for different pupil sizes and different wavelengths and the final Rx determined based.

In general, the analysis can be applied to other pupil features in addition, or alternatively, to the pupil size. For example, in some embodiment, an Rx can be calculated for different locations of the pupil center relative to the retina of the eye.

An exemplary implementation is described below in conjunction with FIGS. 3-12.

Consider the case of an eye having an amount of spherical aberration as the only non-zero wavefront aberration. Spherical aberration is a fourth order wavefront aberration and can then be expressed as $W(r,\theta)=a_{12}Z_{12}(r,\theta)$, where $Z_{12}=\sqrt{5}(6r^4-6r^2+1)$ is the Zernike polynomial associated with spherical aberration and r is the normalized radius. In this case, as shown by the Zernike polynomial $Z_{12}$, the aberration does not depend on the azimuthal angle θ it is therefore assumed the optimum Rx does not contain any astigmatism corrections, and further that the resulting point spread function is also angle independent. In general, the point spread function is the Fourier transform of the wavefront error, and shares similar symmetry properties as the wavefront error.

For simplicity, in this example, the merit function for the eye is set equal to the normalized intensity of the image at the center of the point spread function. These assumptions reduce the optimization (i.e., search for the maximum of the merit function) to a one dimensional search for the mean power of the correction.

Assume a wavelength of 0.55 microns for the light, and a value for the spherical aberration of $a_{12}=0.097$ microns for a 4 mm pupil. The merit function as a function of the mean power and pupil diameter is contoured in the plot shown in FIG. 3.

Figure 3:
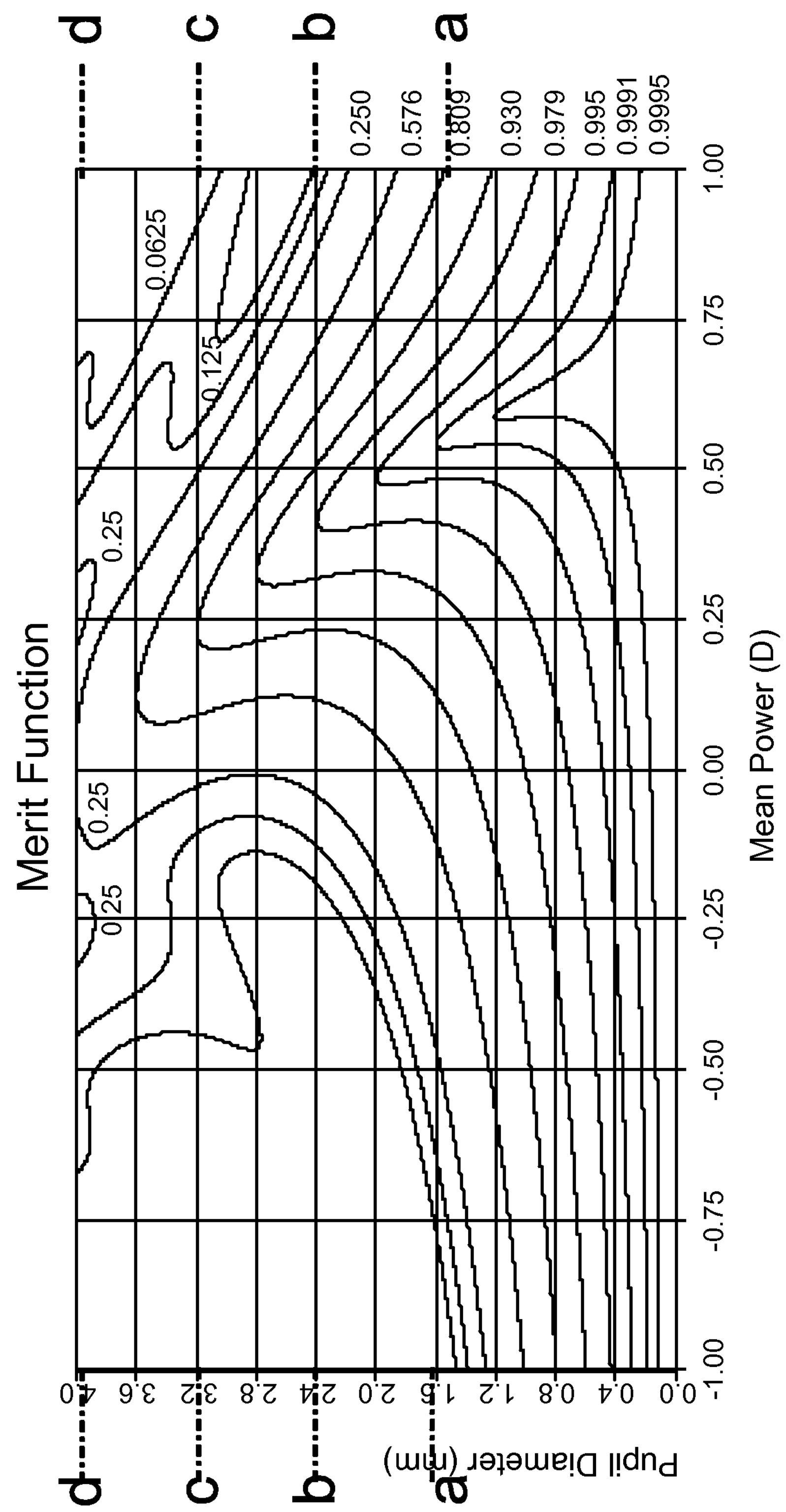
FIG. 3 shows a contour plot of merit function value as a function of pupil diameter and mean power.

The labeled contours in FIG. 3 are not evenly spaced. The contour levels are chosen to correspond to the peak values of the merit function at selected pupil diameters. The plots shown in FIGS. 4A-4D represent sections of the contour plot shown in FIG. 3 and represent the merit function as a function of mean power for fixed pupil diameters of 1.6 mm, 2.4 mm, 3.2 mm and 4.0 mm, respectively, where 4.0 mm is the maximum pupil diameter for this eye. The locations of these horizontal cuts are also indicated in FIG. 3.

Conventionally, the search algorithm for the Rx for this eye would be determined using information for a single large pupil size, such as 4.0 mm. As is evident from FIG. 4D, the merit function for the full 4.0 mm pupil has three peaks of equal height, separated by more than a quarter of a diopter. Unfortunately, conventional algorithms offer no rational way to distinguish between these peaks and also offer no guidance as to which peak may be the true peak (peak at the mean power value that provides the best vision), leading to the selection of a non-optimal maximum instead of an optimal maximum in some cases.

Figure 4A:
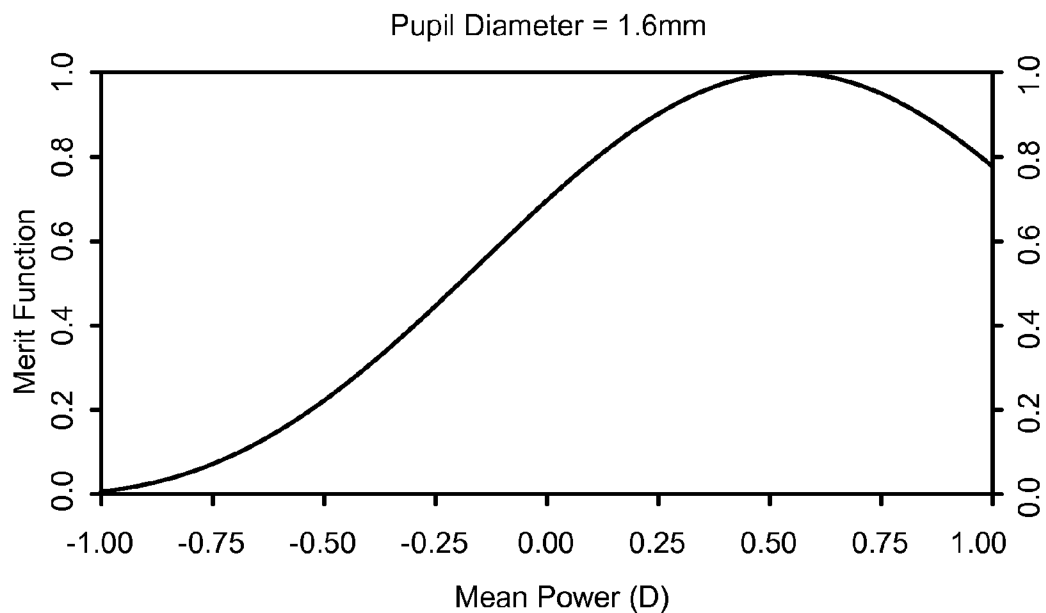
FIGS. 4A-4D show plots of merit function value as a function of mean power for pupil diameters of 1.6 mm, 2.4 mm, 3.2 mm, and 4 mm, respectively, of the merit function surface shown in FIG. 3.
Figure 4B:
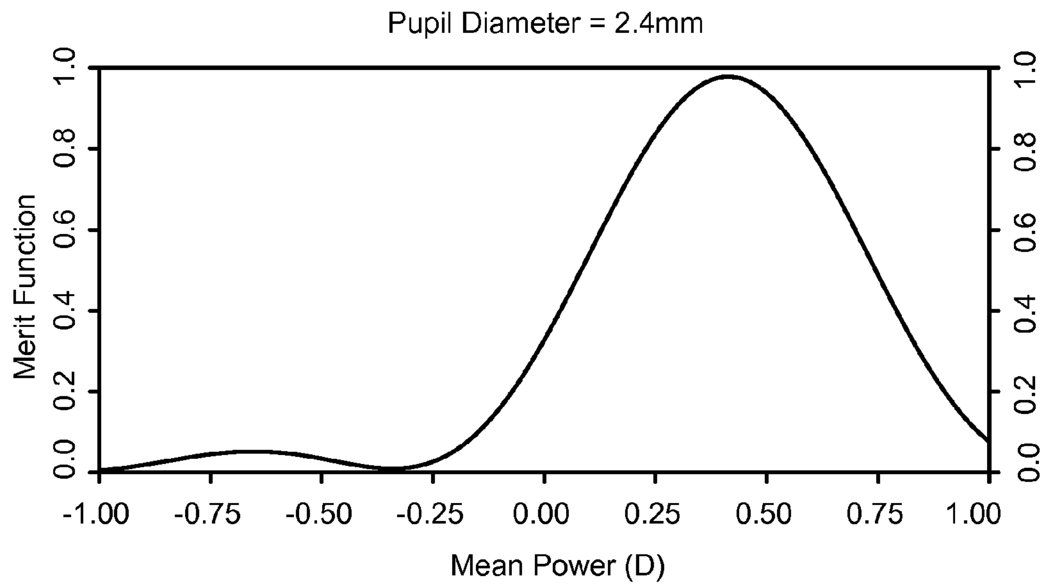
Figure 4C:
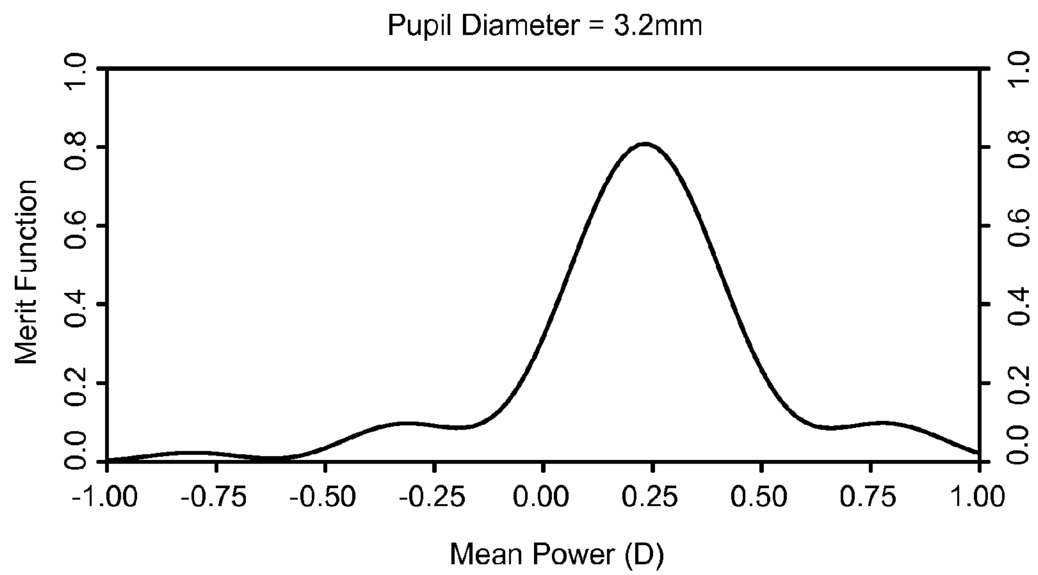
Figure 4D:
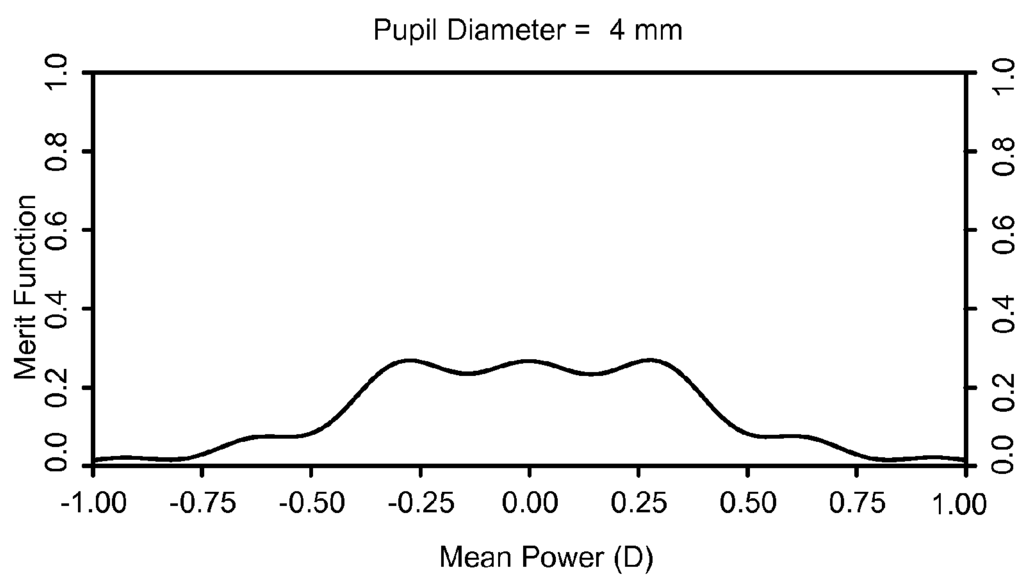

However, at smaller pupil sizes, e.g., 1.6 mm and 2.4 mm, the merit function has a single distinct maximum as evident in FIGS. 4A and 4B. Thus, using the above-described methods, one can identify the correct peak (and hence, Rx) at the 4.0 mm pupil diameter as follows. The variable pupil search starts by calculating the best Rx for a very small pupil (e.g., 0.5 mm). In the limit as the pupil diameter approaches zero there is no ambiguity in the correct Rx, since the second order correction is completely determined by the local curvature of the wavefront error. For this example the central curvature implies a mean power of 0.65 diopters.

Figure 5:
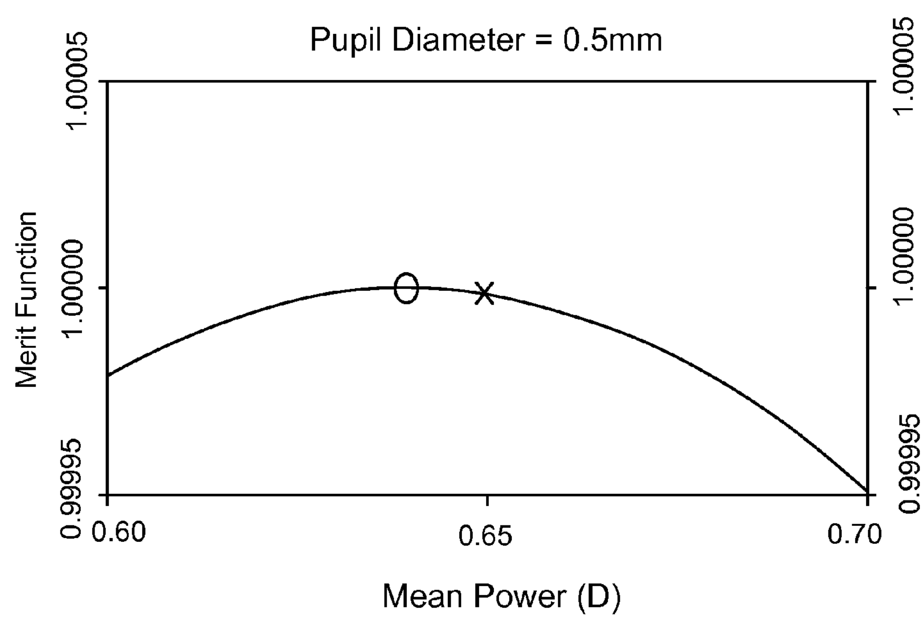
FIG. 5 shows a plot of merit function value as a function of mean power for a pupil diameter of 0.5 mm.

A basic step in the algorithm is illustrated in FIG. 5, which shows the merit function as a function of mean power over the range of mean powers from 0.60 to 0.70 for a pupil diameter of 0.5 mm. The mean power value of the previous uniquely determined Rx is 0.65. The merit function is evaluated at that location (i.e., for mean power of 0.65) and marked with an X in FIG. 5. An assumption of this search algorithm is that the "true" peak at this new diameter is located directly "uphill", in the direction of increasing merit function, from the Rx obtained at the previous diameter, which serves as the initial "guess" Rx at the current (larger) diameter. In this example, searching for the mean power in the direction of increasing merit function (i.e., "walking the solution uphill") locates the peak at about 0.64 diopters, marked with an O in FIG. 5. For this step from the smallest pupil diameter to a pupil diameter of 0.5 mm, the search only spanned over a range of mean power values of 0.01 diopters. The part of the curve outside of the region between the X and the O is not sampled by the search algorithm, and is shown in FIG. 5 only for clarity.

After the steps described above are repeated a number of times for progressively increasing pupil diameters out to a pupil diameter of 3.0 mm, a peak with a mean power of 0.28 diopters is found. As the value of the pupil diameters increase, the step size to the next diameter may decrease, since the additional area from the increase in the pupil diameter increases as the square of the pupil diameter. Decreasing the step size ensures that the increase in area between steps remains constant.

Figure 6:
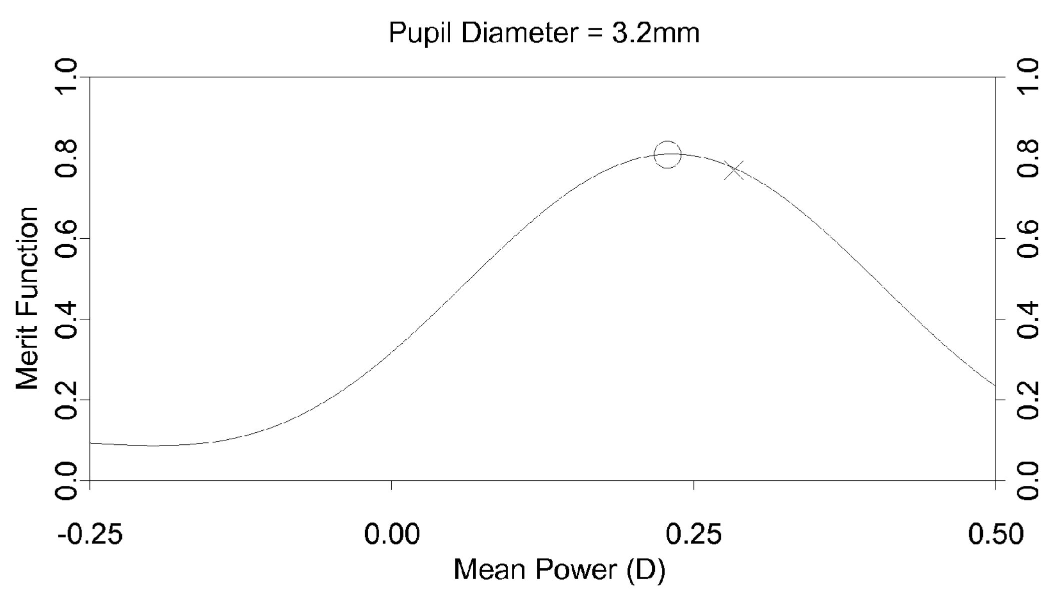
FIG. 6 shows a plot of merit function value as a function of mean power for a pupil diameter of 3.2 mm.
Figure 7A:
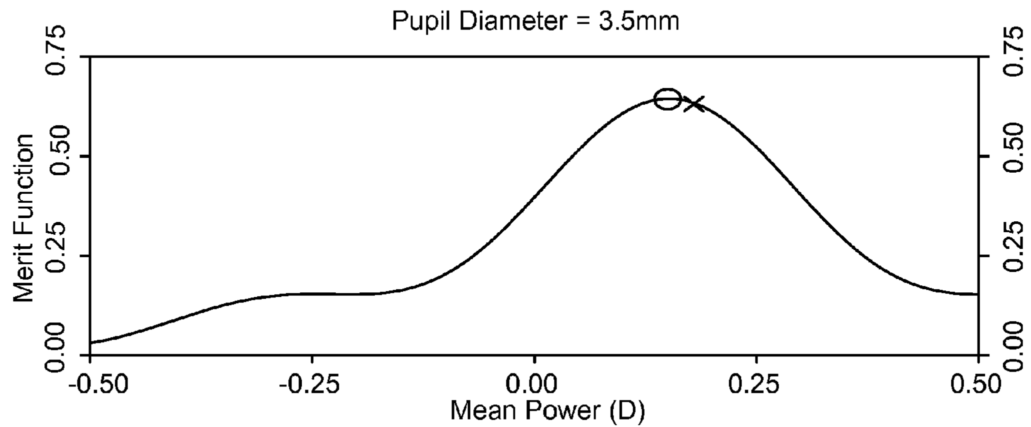
FIGS. 7A-7F show plots of merit function value as a function of mean power for pupil diameters 3.5 mm, 3.6 mm, 3.7 mm, 3.8 mm, and 4.0 mm, respectively.
Figure 7C:
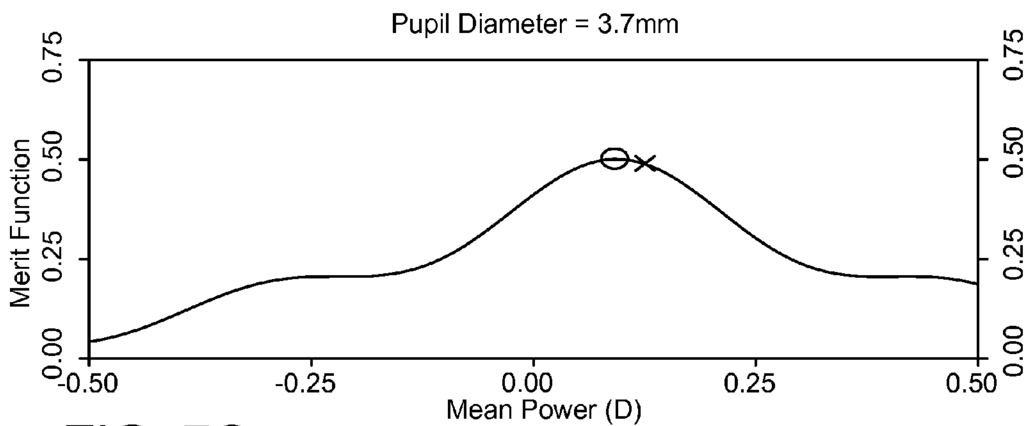
Figure 7E:
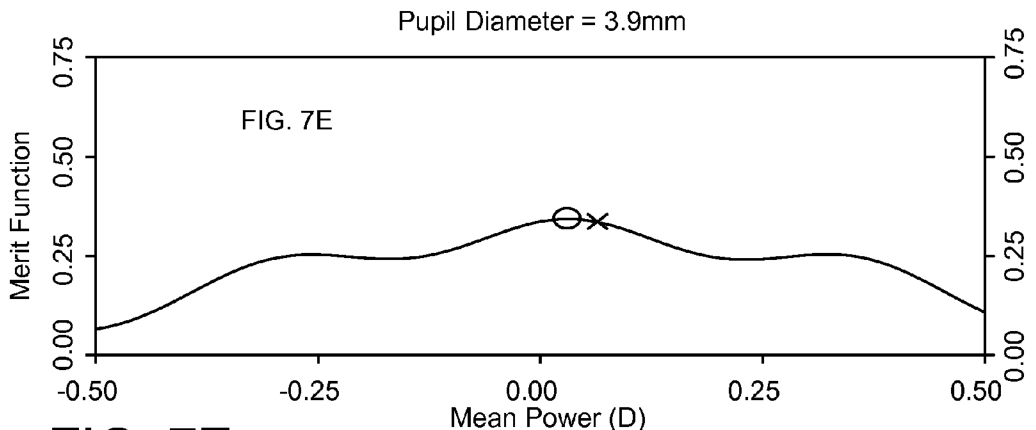
Figure 7B:
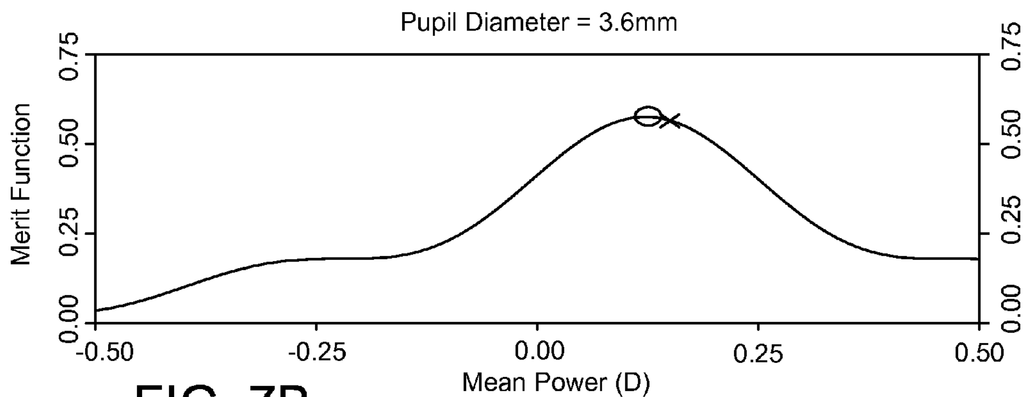
Figure 7D:
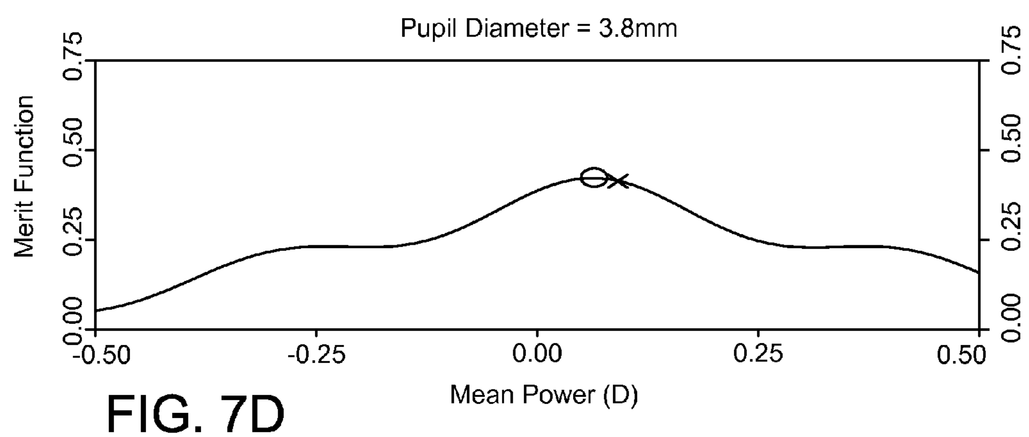
Figure 7F:
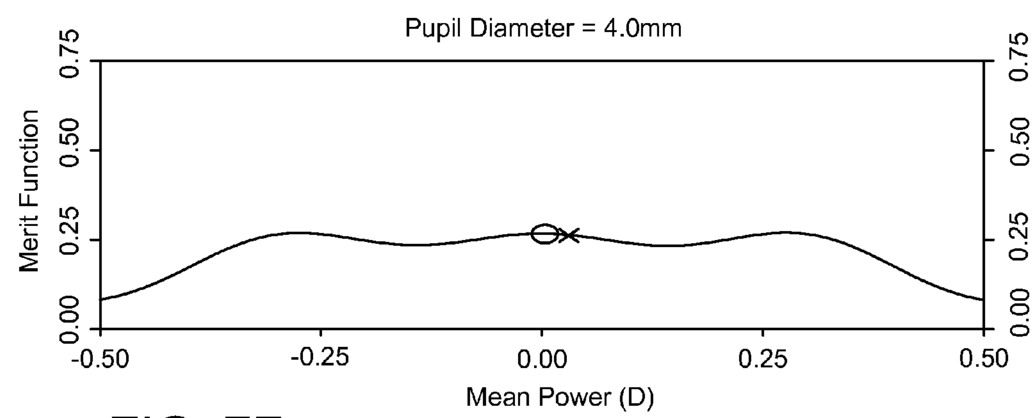

A plot of the merit function as a function of mean power shown in FIG. 6 illustrates the search algorithm step between pupil diameters of 3.0 mm and 3.2 mm. Here, the scale has been expanded to show mean powers from −0.25 to 0.5. In this case the search runs from the X at 0.28 diopters of the Rx at 3.0 mm to the O at 0.23 diopters, a range of only 0.05 diopters. It is noted however, that at this diameter there is one single peak, so a conventional algorithm should have no problem locating the correct solution.

FIGS. 7A-7F show plots of the merit function as a function of mean power for pupil diameters from 3.5 mm to the maximum 4.0 mm in 0.1 mm steps. For each step at a particular pupil diameter, the algorithm only searches the mean power within the range bounded by X and O, where X represents the merit function value at the Rx from the prior pupil diameter and O is the new peak. As the pupil diameter approaches the maximum 4.0 mm size, the algorithm naturally picks the central peak. The central peak is the peak that is best "connected" to the series of Rxs measured at smaller pupil diameters. The algorithm does not examine the mean power values associated with the other two peaks, i.e., at ~−0.25 diopters and ~0.25 diopters as evident in FIG. 7F.

In general, the two cylindrical components (cylinder and cylinder axis) of the Rx are not necessarily zero, and that the peak of the point spread function (or other metric) is not a central peak. When cylindrical errors cannot be assumed to be zero, the search for the maximum in the merit function should be done in additional dimensions. For example, for the current metric, the search should be done in five dimensions: mean power, cylinder, cylinder axis, the x-coordinate of the peak in the point spread function and the y-coordinate of the peak in the point spread function. Any of a number of efficient search algorithms could be used, for example, the method of steepest descent (ascent). The net result for the general case would be four functions of pupil diameter: the mean power, two cylinder components, and the merit function. In the exemplary implementation described above, only the mean power and merit function are non-trivial. Plots for both of these parameters, as a function of pupil size, are shown in FIGS. 8A and 8B.

The final task is to determine a single, best overall Rx for this eye. One simple solution is to use the Rx for the largest aperture. In this example, the correction obtained for an eye with the 4.0 mm pupil diameter aperture would be 0.00 diopter, that is, no correction.

One advantage of this algorithm is the possibility of combining the result of the full range of possible pupil sizes to derive an Rx. For example, the method enables the determination of an Rx that provides the best possible vision under specific, ideal viewing conditions for the wearer.

Figure 8A:
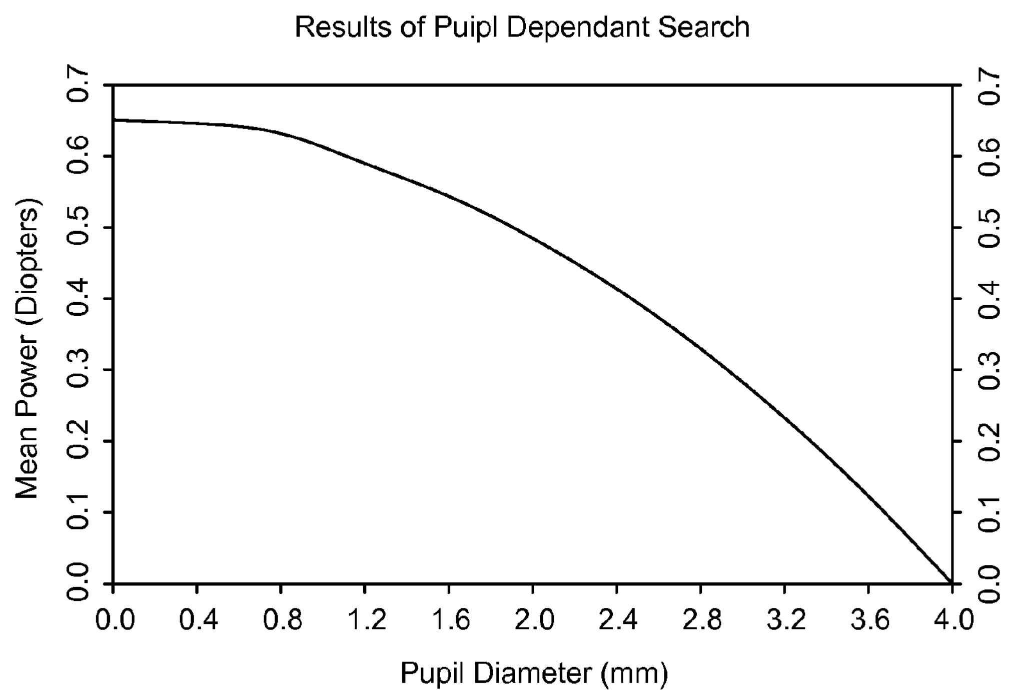
FIGS. 8A and 8B show plots of mean power and merit function value, respectively, as a function of pupil diameter.
Figure 8B:
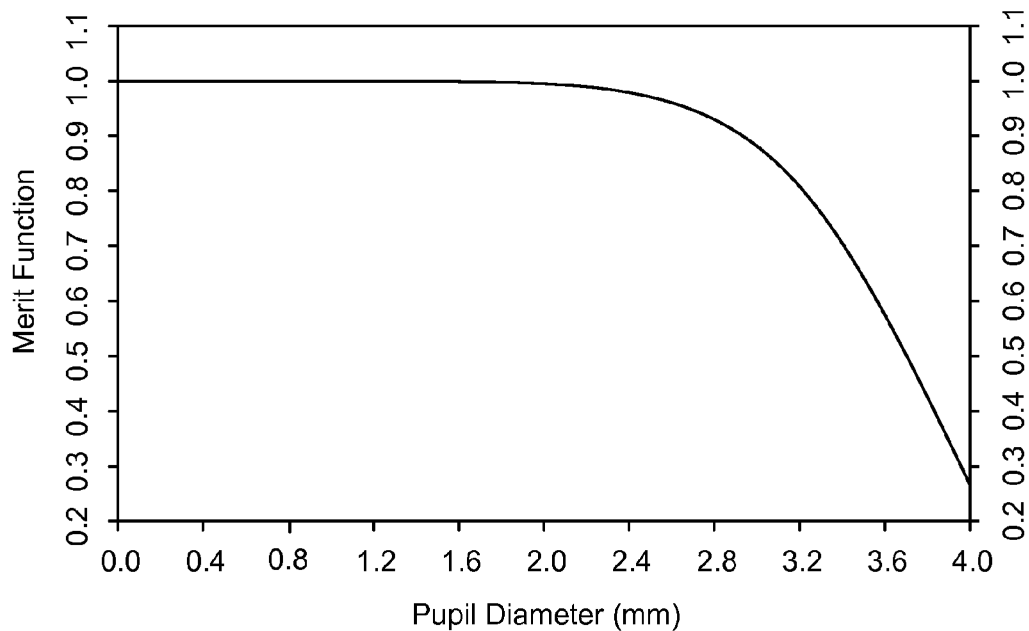

As is evidence from the plots shown in FIGS. 8A and 8B, the highest values of the merit function are obtained for the smallest apertures. The bias towards smaller aperture sizes is a result of using a merit function that is a "normalized" metric. This normalized metric measures the performance of the system at a particular pupil diameter having only second order corrections relative to the best possible performance at that particular pupil diameter. For example, the normalized metric may be the Strehl ratio, which is proportional to the ratio of the peak of the point spread function (with second order corrections) to the maximum peak possible when no aberration is present. For asymptotically small apertures, all aberrations can be eliminated using only second order corrections. On the other hand, for larger apertures, higher order correction terms need to be taken into account in order to achieve an aberration-free system. As a result, the value of the normalized metric decreases for larger pupil diameters.

To counteract this bias, the merit function in the above plot can be rescaled to represent the peak intensity of the focus by taking into account the full area of the pupil. The simple scaling of multiplying the merit function with the square of the pupil diameter (to normalize the system with the square of the maximum pupil size) may be considered a measure of the overall performance of the lens eye combination.

Figure 9:
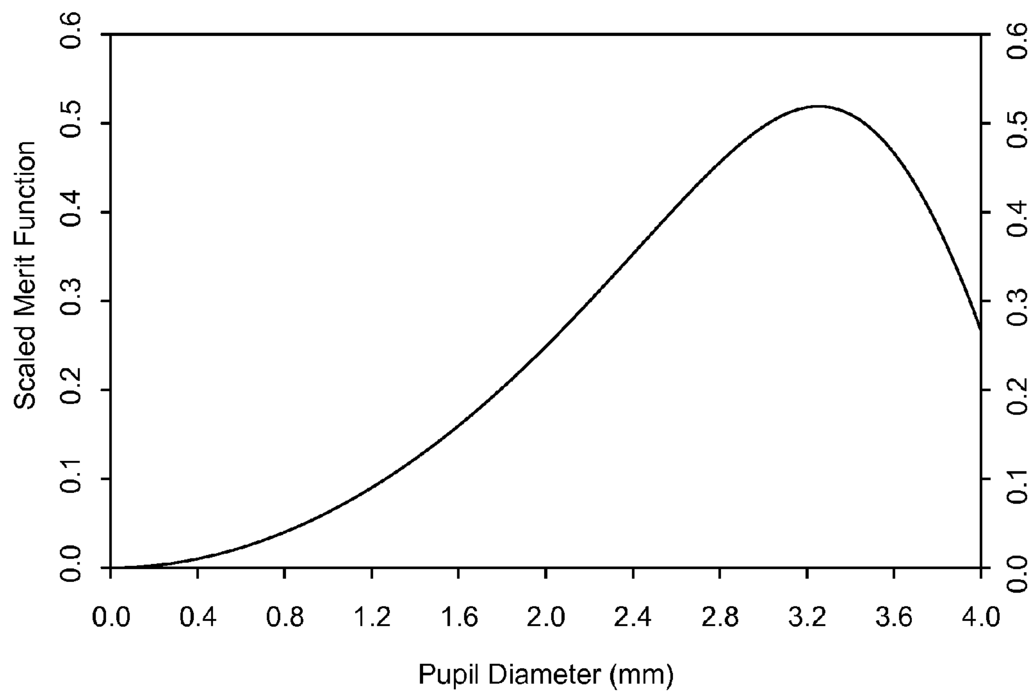
FIG. 9 shows a plot of a scaled merit function value as a function of pupil diameter.

The curve generated from such a procedure is shown in FIG. 9. This curve peaks around 3.25 mm. The Rx at that diameter can be read off of the previous plot, and is about 0.22 diopters.

As discussed previously, another possible criterion for determining the best Rx is to find the Rx that performs best, on average, over the full range of pupil diameters. In order to evaluate the results based on this criterion, the fact that the smaller pupil diameters have greater depths of focus; i.e., the width of the plot of the merit function as a function of mean power gets narrower for larger pupils should be taken into account. A greater depth of focus also means that the merit function maintains a high value over a larger range of mean power, thus having a wider width. A simple model that takes into account the effect of depth of focus is to set the width of the merit function curve as being inversely proportional to the square of the pupil diameter. In addition, the value of the scaled merit function represents the effective area of the lens, as opposed to the original normalized merit function which is a function of the normalized intensity of the image at the center of the point spread function, as described above. The net result is that the width of the scaled merit function is roughly inversely proportional to the product of the peak of the (initial) normalized merit function and the square of the pupil diameter.

Figure 10:
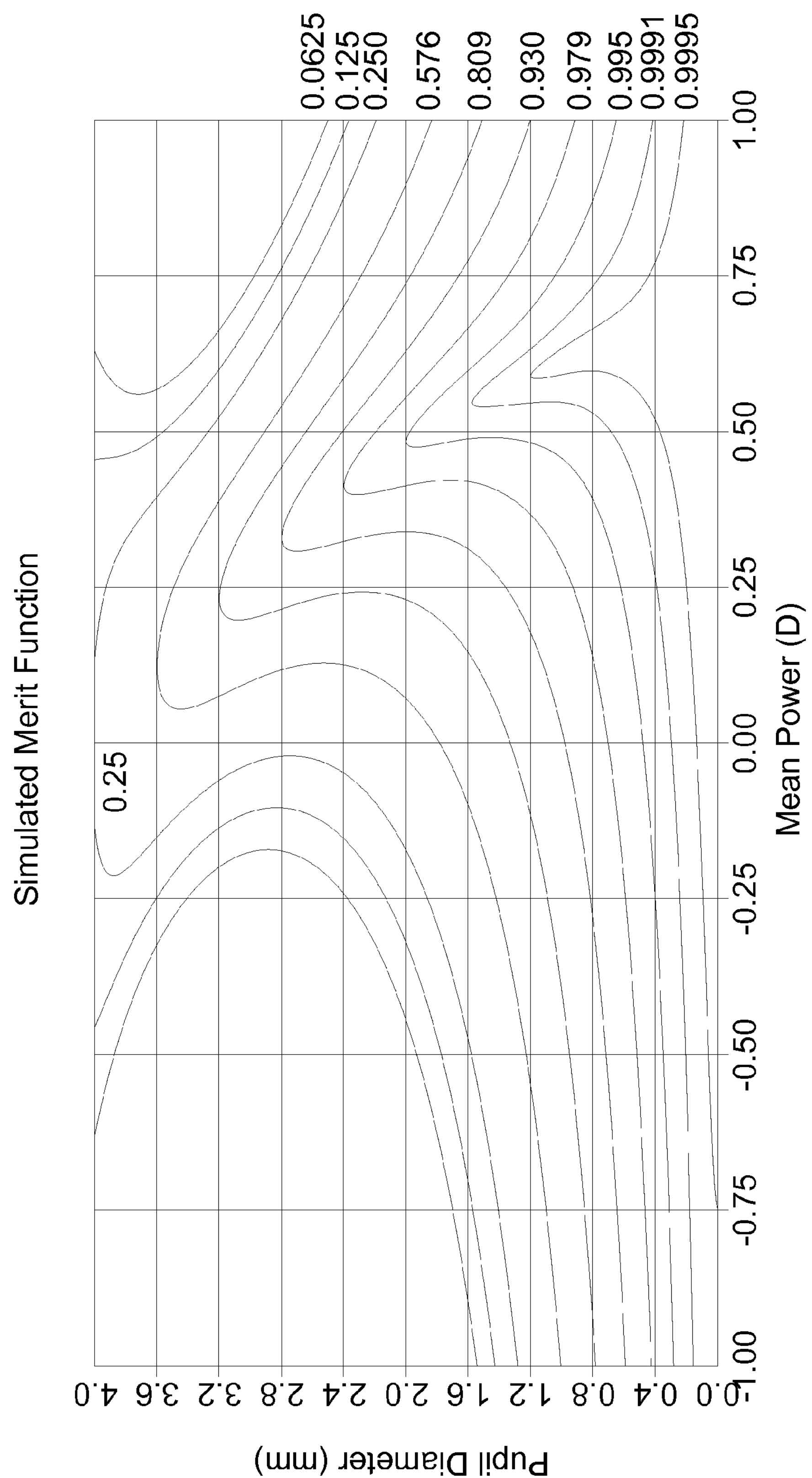
FIG. 10 shows a contour plot of a simulated merit function as a function of mean power and pupil diameter.
Figure 11:
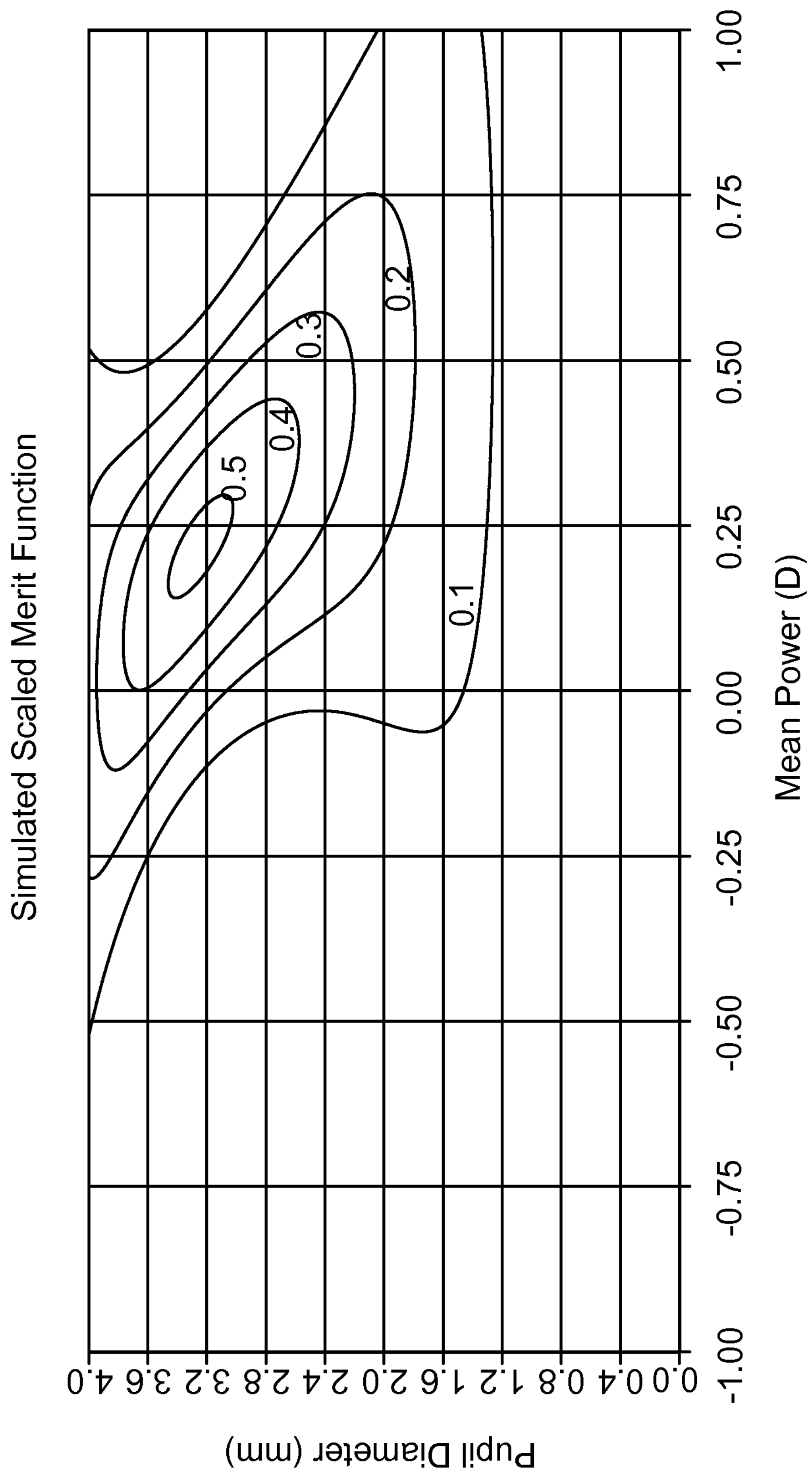
FIG. 11 shows a contour plot of a simulated scaled merit function as a function of mean power and pupil diameter.

FIG. 10 is a simulation of the contour plot shown in FIG. 3, constructed entirely from the mean power and merit function plots shown in FIGS. 8A and 8B. The equation for the simulated two-dimensional merit function M shown in FIG. 10 is given by:

$$M(mp,d)=\exp(-(mp-mp_0(d))^2/2\sigma(d)^2),$$

where mp and d are the mean power and diameter values, $mp_0(d)$ is the mean power as a function of diameter curve shown above in FIGS. 8A and 8B, $\sigma(d)=1.58/(m(d)(d/4)^2)$, m(d) is the peak merit function as a function of diameter shown in FIG. 8B, and 1.58 is a scale factor determined empirically. σ is a parameter related to the width of the merit function. The contour plot shown in FIG. 10 matches the original full calculation shown in FIG. 3 very well, except for the absence of the extra "side-lobes" at large pupil diameter.

The same reasoning can be applied to turn the information contained in FIG. 10 into an absolute measure of image quality, rather than one normalized by diameter, by scaling the simulated merit function shown in FIG. 10 with the square of the pupil diameter. The result is shown below in FIG. 11, contoured at regular intervals.

Figure 12:
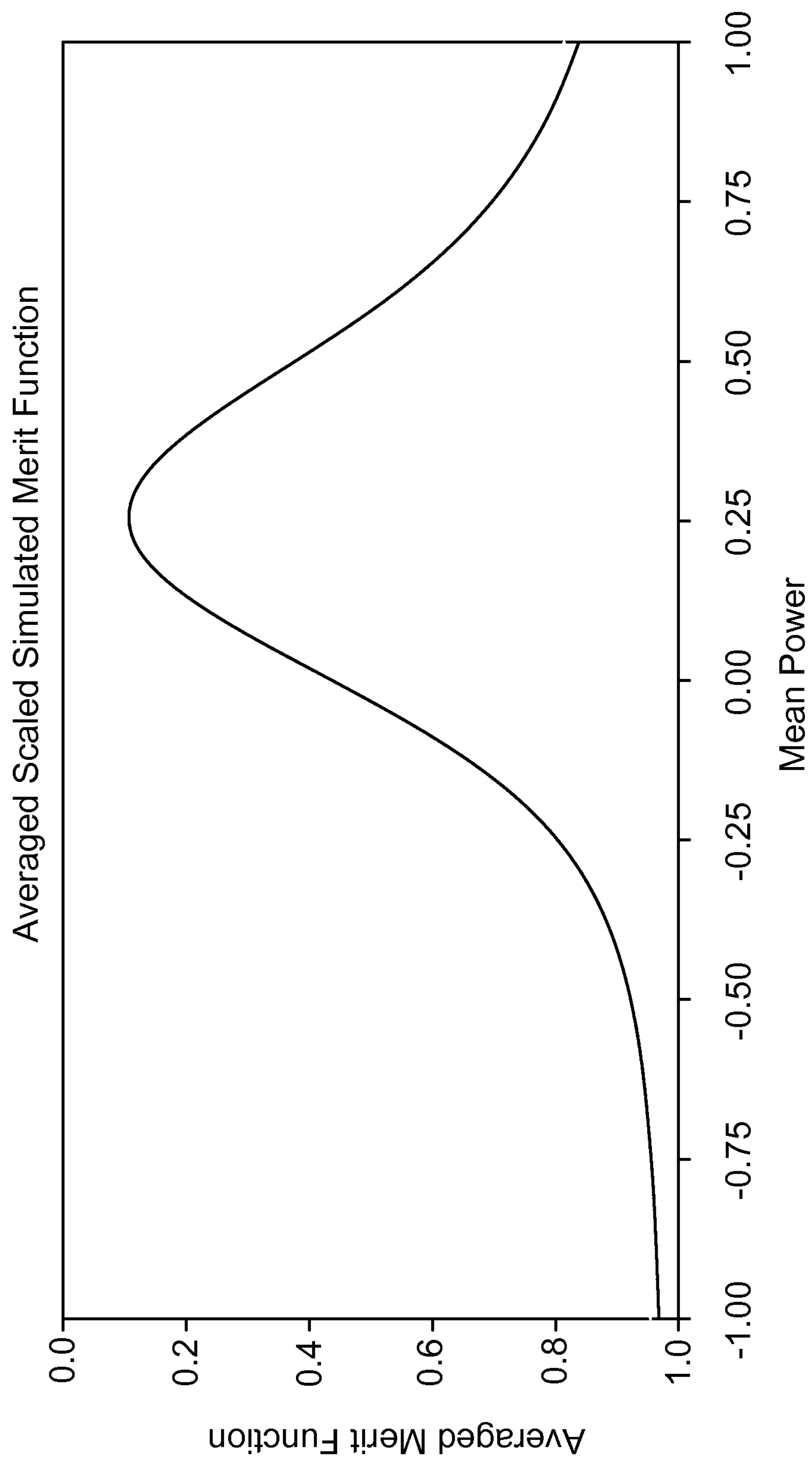
FIG. 12 shows a plot of an averaged scaled simulated merit function as a function of mean power.

As a measure of the average vision quality over all pupil diameters, the function can be integrated over the pupil diameter. The resulting curve is shown in FIG. 12. Here, the curve has a peak at a mean power of 0.25 diopters, indicating another possible "best" Rx for the wearer, based on the data gathered across all the measured pupil diameters.

Variations to the exemplary implementation described above may involve using other types of merit function besides that of a normalized intensity of the image at the center of the point spread function. For example, a reciprocal of the RMS width of the point spread function or the curvature of the wavefront may be used as the merit function. The initial pupil size may also be separately determined, and may not rely on a unique, analytical determination as shown in the exemplary implementation. The step size between different pupil diameters may also be independently selected or be defined by the user. The evaluation matrix for determining the final Rx may also be selected based on the nature of the correction—the Rx may be selectively weighted for larger pupil diameters for night lenses, or selected weighted for small pupil diameter for daylight lenses. In addition, the merit function may be evaluated at different points along the path of the propagation of light, instead of only at the image plane of the eye (retina).

Figure 13:
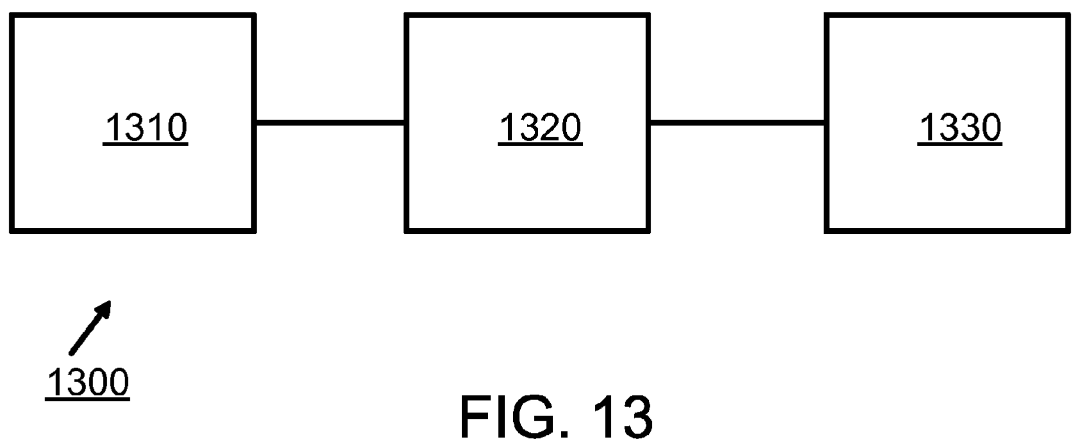
FIG. 13 is a schematic diagram of a system for determining an Rx and manufacturing an ophthalmic lens based thereon.

Referring to FIG. 13, a system 1300 used to perform a refraction on a patient, establish an Rx and manufacture ophthalmic lenses based on the Rx includes a measuring device 1310, a data processing unit 1320, and a production unit 1330. Measuring device 1310 is used to determine a wavefront aberration of an eye (or eyes) for the patient. In general, a variety of measuring devices can be used, such as a wavefront sensor (e.g., aberrometer). For example, a Shack-Hartmann wavefront sensor can be used. Wavefront sensors are available commercially from Abbott Medical Optics (Santa Ana, Calif.), Carl Zeiss Meditec (Dublin, Calif.), and Alcon (Fort Worth, Tex.), for example.

Data processing unit 1320 is arranged to receive information about the wavefront aberration of the eye from measuring device 1310 and to process this information to provide using the methods described above to and output the Rx. Generally, a variety of different data processing units can be used. Such units can include one or more electronic processors in communication with a non-volatile computer readable medium storing instructions for carrying out the algorithm.

Data processing unit 1320 can be a computer, either standalone or networked. In some embodiments, data processing unit 1320 and measuring device 1310 are part of the same system, and the electronic processor(s) of the data processing unit are used to both analyze the wavefront information acquired using the measuring device to produce information about the aberrations of the eye, and to process that information to provide the Rx.

The Rx output by the data processing unit 1320 is delivered to production unit 1330, which produces an ophthalmic lens based on the design. Production unit 1330 can be a conventional unit (e.g., a commercially available production unit). In some embodiments, measuring device 1310, data processing unit 1320, and production unit 1330 are all part of a single integrated product that can be installed in a single location (e.g., an ophthalmic professional's office or lab). In certain embodiments, measuring device 1310, data processing unit 1320, and production unit 1330 are all different products, in communication with each other via a communications network (e.g., the internet).

In general, the methods described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on a computer storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

Other embodiments are in the claims

What is claimed is:

1. A method of determining an ophthalmic prescription (Rx) for a patient's eye, comprising:

obtaining a wavefront measurement of the patient's eye;

determining a first Rx for the patient's eye from the wavefront measurement, the first Rx corresponding to a maximum value of a merit function calculated from the wavefront measurement of the patient's eye for a first size of the pupil of the patient's eye;

determining one or more additional Rx's of the patient's eye for one or more additional pupil sizes different from the first pupil size, wherein each additional Rx is determined for a corresponding size by calculating a value of the merit function for the previously-calculated Rx at the corresponding size and searching for an Rx at the corresponding size that provides a larger value of the merit function than the previously-calculated Rx at the corresponding size;

determining, using a processor, a final Rx based on the first Rx and the additional Rx's; and outputting the final Rx.

2. The method of claim 1, wherein each Rx is calculated for the same location of the patient's eye.

3. The method of claim 2, wherein the location is a central location of the patient's eye.

4. The method of claim 1, wherein the first size is a smaller size than the one or more additional sizes.

5. The method of claim 1, wherein each of the one or more additional Rx's is determined for a pupil size that is larger than the size used to calculate the prior Rx.

6. The method of claim 1, further comprising ordering an eyeglass lens or contact lens for the patient based on the final Rx.

7. The method of claim 1, further comprising making an eyeglass lens or contact lens for the patient based on the final Rx.

8. The method of claim 1, wherein calculating the Rx's comprise accounting for one or more physiological aspects of the patient's eye.

9. The method of claim 8, wherein one of the physiological aspects is the Stiles-Crawford effect.

10. The method of claim 8, wherein one of the physiological aspects is accounting for a preferential axis orientation.

11. The method of claim 10, wherein the preferential axis orientation is 0 degrees or 90 degrees.

12. The method of claim 10, wherein accounting for the preferential axis orientation comprises weighting the orientation more heavily than other orientations in the determining the final Rx.

13. The method of claim 1, wherein the wavefront measurement comprises information about the wavefront aberrations of the eye.

14. The method of claim 1, wherein the wavefront measurement for the patient's eye is measured for a pupil that has a relatively large size compared to the first size.

15. The method of claim 1, wherein obtaining the wavefront measurement comprises obtaining a wavefront measurement for a pupil that has a relatively large size compared to the first size, and modifying the wavefront measurement to correspond to smaller size pupil.

16. The method of claim 1, wherein obtaining the wavefront measurement comprises obtaining a plurality of wavefront measurements of the eye each corresponding to a different pupil size.

17. The method of claim 1, wherein the final Rx is the Rx corresponding to the largest pupil size.

18. The method of claim 1, wherein determining the final Rx comprises calculating an Rx based on the first Rx and additional Rx's.

19. The method of claim 17, wherein at least some of the first Rx and the additional Rx's are weighted differently in the calculation of the final Rx.

20. The method of claim 18, wherein the Rx's are weighted based on anticipated use of the Rx by the patient.

21. The method of claim 1, wherein the merit function corresponds to a metric related to a caustic of a light ray passing through a corrective optic and the eye.

22. A non-transitory computer readable storage medium encoded with executable instructions comprising:

instructions operable on a processor to determine a first ophthalmic prescription (Rx) for a patient's eye from a wavefront measurement of the patient's eye, the first Rx corresponding to a maximum value of a merit function calculated from the wavefront measurement for the patient's eye for a first size of the pupil of the patient's eye;

instructions operable on a processor to determine one or more additional Rx's for the patient's eye for one or more additional pupil sizes different from the first pupil size, wherein each additional Rx is determined for a corresponding size by calculating a value of the merit function for the previously-calculated Rx at the corresponding size and searching for an Rx at the corresponding size that provides a larger value of the merit function than the previously-calculated Rx at the corresponding size;

instructions operable on a processor to determine a final Rx based on the first Rx and the additional Rx's; and instructions operable on a processor to output the final Rx.

23. A system for determining a prescription (Rx) for a patient's eye, the system comprising:

a processor, and the non-transitory computer readable storage medium encoded with executable instructions of claim 22, wherein during operation the processor executes the instructions stored on the storage medium and the system outputs the final Rx.

24. A method for manufacturing an ophthalmic lens, comprising:

determining an ophthalmic prescription for a patient's eye using the method of claim 1; and forming the ophthalmic lens based on the final Rx.

25. A method of forming an ophthalmic prescription (Rx) for a patient's eye, comprising:

obtaining a wavefront measurement of the patient's eye;

determining a first Rx for the patient's eye from the wavefront measurement, the first Rx corresponding to a maximum value of a merit function calculated from the wavefront measurement of the patient's eye for a first size of the pupil of the patient's eye;

determining one or more additional Rx's of the patient's eye for one or more additional pupil sizes different from the first pupil size, wherein each additional Rx is determined for a corresponding size by calculating a value of the merit function for the previously-calculated Rx at the corresponding size and searching for an Rx at the corresponding size that provides a larger value of the merit function than the previously-calculated Rx at the corresponding size;

determining a final Rx based on the first Rx and the additional Rx's;

outputting the final Rx; and forming an ophthalmic lens based on the final Rx.

* * * * *

UNITED STATES PATENT AND TRADEMARK OFFICE

CERTIFICATE OF CORRECTION

PATENT NO. : 8,777,414 B2
APPLICATION NO. : 13/721471
DATED : July 15, 2014
INVENTOR(S) : Ray Steven Spratt et al.

It is certified that error appears in the above-identified patent and that said Letters Patent is hereby corrected as shown below:

On the Title Page, Col. 1, (71) Applicants, line 3, delete “Aclen” and insert -- Aalen --.

In the Drawings

On Sheet 10, FIG. 8A, line 1, delete “Puipl” and insert -- Pupil --.

In the Specification

In Col. 1, line 10, delete “Jul. 16, 2009.” and insert -- Jul. 16, 2010. --.

In Col. 4, line 44, delete “algorthims” and insert -- algorithms --.

Signed and Sealed this
Twenty-first Day of October, 2014

Michelle K. Lee

Michelle K. Lee
*Deputy Director of the United States Patent and Trademark Office*